(12) United States Patent
Kassel et al.

(10) Patent No.: US 9,463,258 B2
(45) Date of Patent: *Oct. 11, 2016

(54) SANITIZING DEVICE

(71) Applicant: Healthy Sole, LLC., Incline Village, NV (US)

(72) Inventors: Robert Kassel, Incline Village, NV (US); Brad Hollander, Minden, NV (US)

(73) Assignee: HEALTHY SOLE, LLC, Incline Village, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,771

(22) Filed: Dec. 11, 2015

(65) Prior Publication Data

US 2016/0089461 A1    Mar. 31, 2016

Related U.S. Application Data

(63) Continuation of application No. 14/249,185, filed on Apr. 9, 2014, now Pat. No. 9,211,352.

(51) Int. Cl.
| | |
|---|---|
| *A61L 2/10* | (2006.01) |
| *A61L 2/20* | (2006.01) |
| *A47L 23/02* | (2006.01) |
| *A61L 2/24* | (2006.01) |

(52) U.S. Cl.
CPC .................. *A61L 2/10* (2013.01); *A47L 23/02* (2013.01); *A61L 2/202* (2013.01); *A61L 2/24* (2013.01); *A61L 2202/26* (2013.01)

(58) Field of Classification Search
CPC ........... A61L 2/10; A61L 2/202; A61L 2/24; A61L 2202/26; A61L 2/0011; A61L 2/08; A61L 2202/14; A61L 2/26; A47L 23/02; A61B 50/20
See application file for complete search history.

(56) References Cited

U.S. PATENT DOCUMENTS

| | | |
|---|---|---|
| 5,668,067 A | 9/1997 | Araujo et al. |
| 5,735,921 A | 4/1998 | Araujo et al. |
| 6,614,039 B2 | 9/2003 | Hollander |

(Continued)

FOREIGN PATENT DOCUMENTS

| | | |
|---|---|---|
| JP | 2006068028 | 3/2006 |
| WO | WO0062823 | 10/2000 |

OTHER PUBLICATIONS

References cited in U.S. Appl. No. 14/249,185, filed Apr. 9, 2014, the priority of which is claimed.

*Primary Examiner* — Xiuyu Tai
(74) *Attorney, Agent, or Firm* — Richard C. Litman

(57) ABSTRACT

The shoe sole sanitizer provides a UV radiation emitting system that kills microbial pathogens deposited on shoe sole surfaces. The system includes a housing containing at least one UV radiation source. Bottom and side portions of the housing are opaque to provide a UV shield while directing the UV upward towards a top housing portion. The top housing portion has a plurality of holes forming an approximate shape of two shoe sole bottoms. The holes allow the UV radiation to escape the housing and target sole surfaces disposed on and over the exterior of the housing top. Each shoe sole approximation area has a pivotal tang that extends therefrom. Shutters attached internally to the tangs extend or limit UV exposure from the top surface depending on the size of the sole disposed on the top. The system is powered by standard AC electrical power or battery sources.

11 Claims, 4 Drawing Sheets

(56) References Cited

U.S. PATENT DOCUMENTS

| | | |
|---|---|---|
| 6,894,299 B2 | 5/2005 | Harrell et al. |
| 7,875,869 B1 | 1/2011 | Shadan |
| 7,960,706 B2 | 6/2011 | Ullman |
| 8,241,565 B1 | 8/2012 | Abdul |
| 8,512,631 B2 | 8/2013 | Kerr |
| 8,617,464 B2 | 12/2013 | Kerr |
| 8,617,479 B2 | 12/2013 | Gil et al. |
| 2006/0147339 A1 | 7/2006 | Hunter et al. |
| 2008/0310996 A1 | 12/2008 | Kim et al. |
| 2009/0314308 A1 | 12/2009 | Kim et al. |
| 2010/0193709 A1 | 8/2010 | Dalton |
| 2012/0045363 A1 | 2/2012 | Gil |

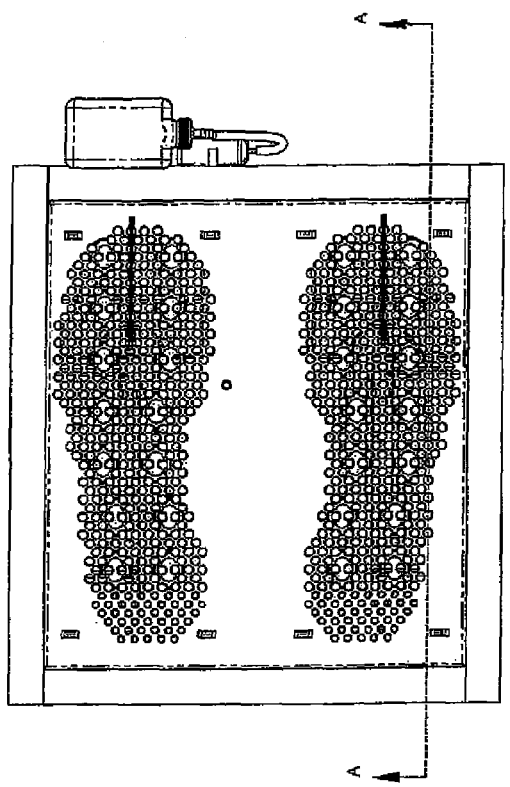
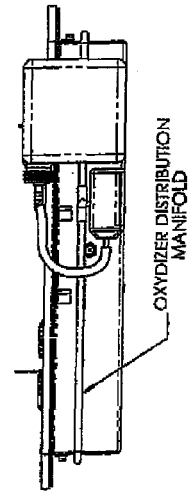
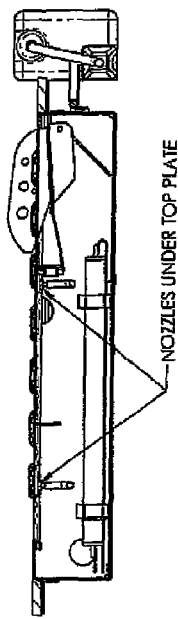

SANITIZING DEVICE

CROSS REFERENCE TO RELATED APPLICATION

This application is a continuation of application Ser. No. 14/249,185, filed Apr. 9, 2014, now U.S. Pat. No. 9,211,352.

BACKGROUND OF THE INVENTION

1. Field of the Invention

The present invention relates generally to sanitizing devices or disinfectant systems, and particularly to a shoe sole sanitizer utilizing ultraviolet radiation and/or advanced oxidation to kill or inactivate microbial pathogens, viruses, bacteria, molds, spores and the like deposited on shoe sole surfaces, hands, feet and other anatomical surfaces.

2. Description of the Related Art

Biocontamination and cross-contamination presents a constantly increasing threat to human and pet health. Bacteria and other microorganisms, which cause infectious diseases, are often spread by persons walking into contaminated areas and then carrying the contaminants to other areas. For example, a person or animal may walk through a contaminated area and his shoes, hooves, paws, socks may pick up bacteria or other microorganisms, which may cause illness, and then the person may grab his shoes by the soles for removal from his feet. The contaminants are then spread from the soles of the shoes to the person's hands or objects that are touched. The health care industry is especially vulnerable to contaminants due to the high likelihood of encountering harmful bacteria and other microorganisms that will cross-contaminate persons and objects. Biocontaminants can spread from the soles of contaminated shoes to carpets and floors, upon which small children and infants crawl. Contaminants can also spread from rest rooms, farms, buildings and/or mass transportation centers.

Thus, sanitizing devices addressing the aforementioned problems are desired.

SUMMARY OF THE INVENTION

The sanitizing device, and in particular a shoe sole sanitizer, provides a UVC and/or advanced oxidation system that kills or inactivates microbial pathogens deposited on the effected surfaces and in particular the shoe sole surfaces, including the side surfaces of a foot or shoe. The system includes a housing containing at least one LTV radiation source and/or advanced oxidation source. Bottom and side portions of the housing are opaque to provide a UV shield and may contain emitters directing the UV upward towards top housing portion. The top housing portion has a plurality of holes or slots or other shaped apertures to emit the germicidial energy; preferably, the apertures form an approximate shape of two shoe sole bottoms. The holes allow the UV radiation to escape the housing and target shoe sole surfaces disposed on and over the exterior of the housing top. In order to increase the effect of the germicidal energy the top housing portion has protrusions or ridges designed throughout the aperture design to raise the shoe or foot above the top housing surface. Additionally, the top housing portion can also be formed as a recessed surface so as to permit the germicidal energy to impact additional side surfaces of the shoe or foot placed thereon in addition to the sole.

The system can be powered by standard AC electrical power or battery sources. Each shoe sole approximation area of the top has a pivotal tang that extends therefrom. A shutter system is attached internally to the tangs thereby extending or limiting UV exposure from the top surface depending on the size of the sole disposed on the top. The shutter system can be at the front of the sole or be shaped to approximate the entire sole bottom or any portion thereof. The shutter system may be a single shield or be segmented shields that encompass any desired design or configuration; and may be deployed singly or jointly.

These and other features of the present invention will become readily apparent upon further review of the following specification and drawings.

BRIEF DESCRIPTION OF THE DRAWINGS

FIG. 4 is a view of the shoe sole sanitizer incorporating an advanced oxidation system therein.

FIG. 4A is a view of the shoe sole sanitizer incorporating an advanced oxidation system therein along lines A-A of FIG. 4.

FIG. 5 is a side view of the shoe sole sanitizer incorporating an advanced oxidation system therein showing the distribution manifold.

Similar reference characters denote corresponding features consistently throughout the attached drawings.

DETAILED DESCRIPTION OF THE PREFERRED EMBODIMENTS

Figure 1:
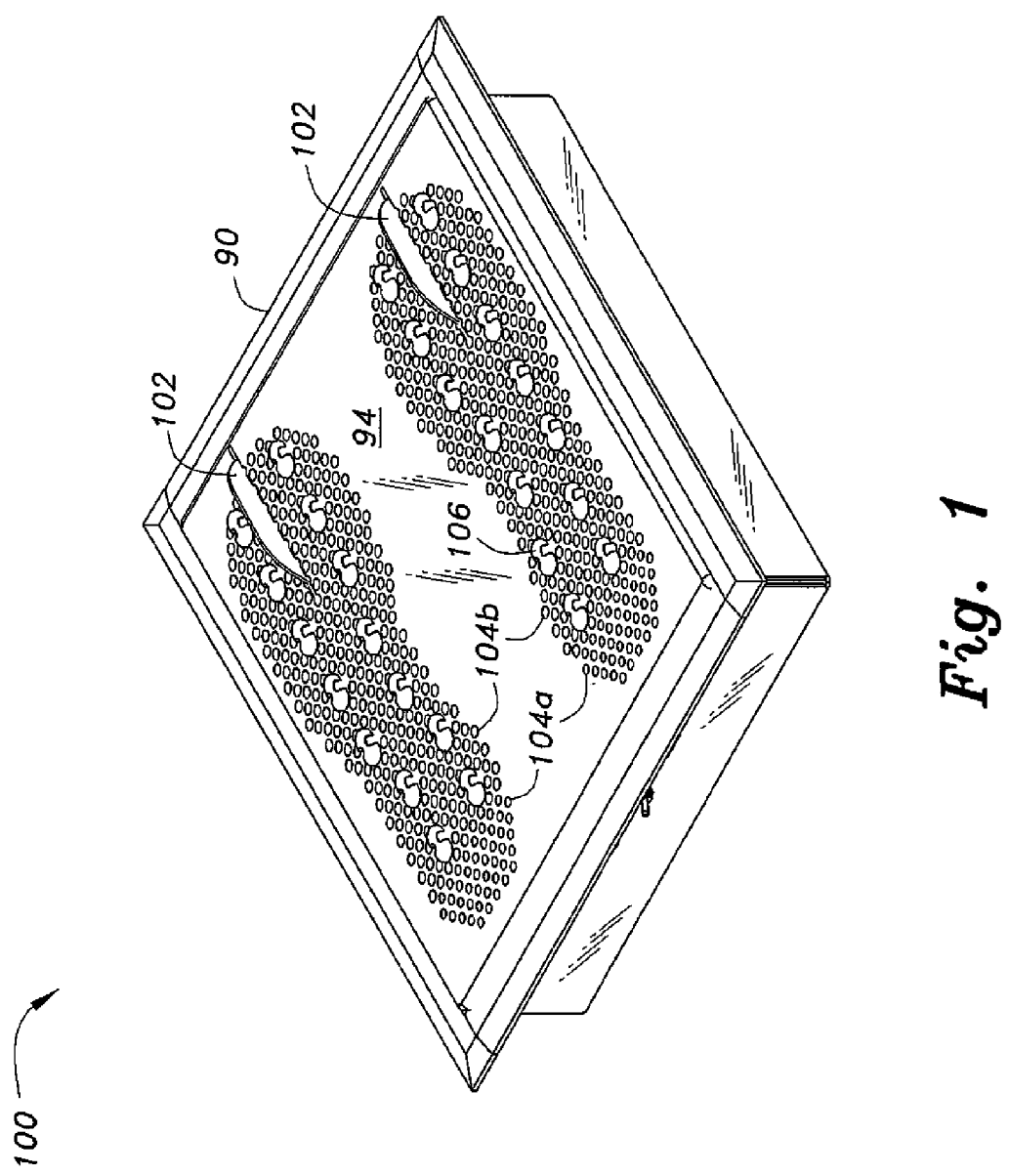
FIG. 1 is a perspective view of the shoe sole sanitizer according to the present invention.
Figure 2:
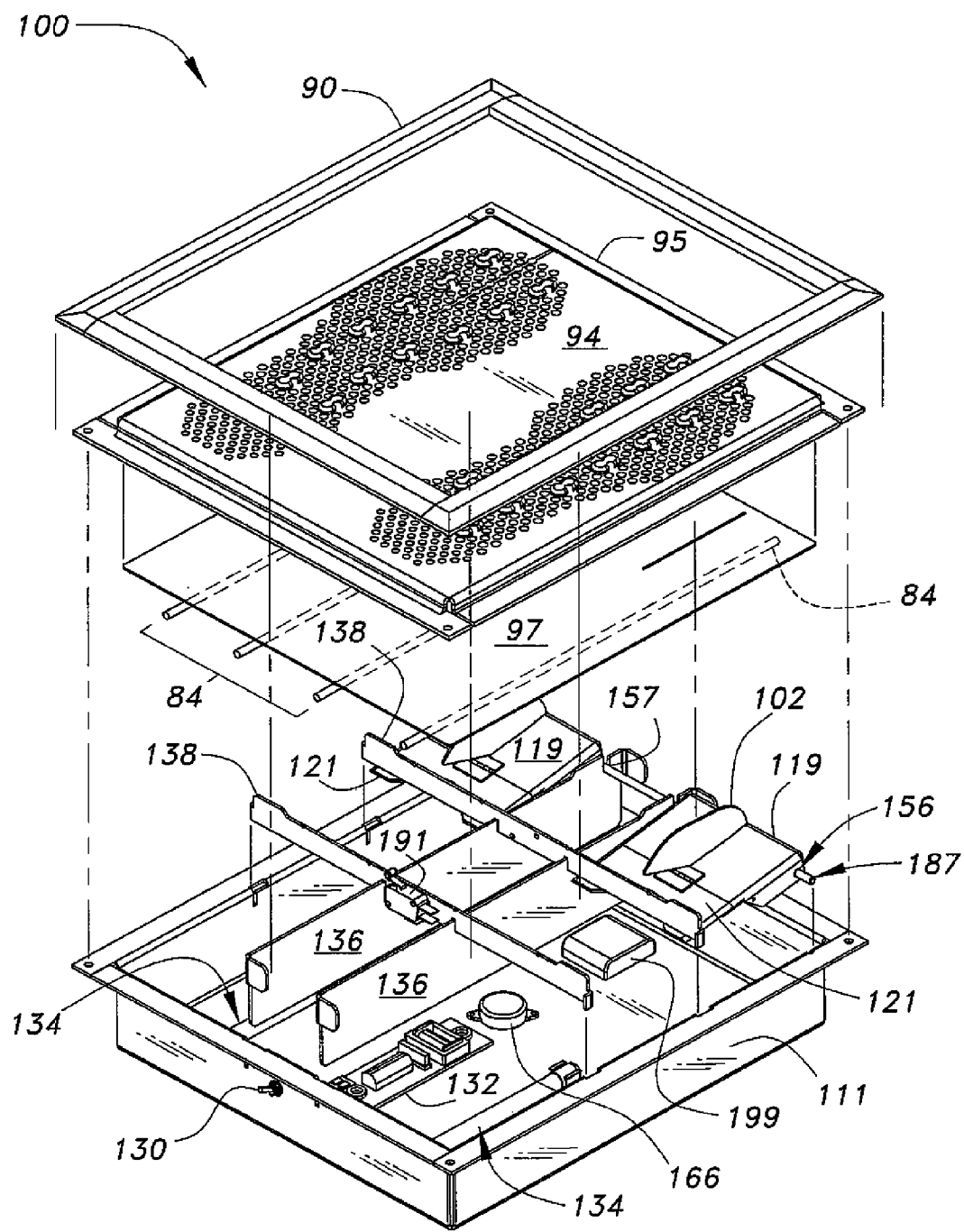
FIG. 2 is an exploded, perspective view of the shoe sole sanitizer according to the present invention.
Figure 3:
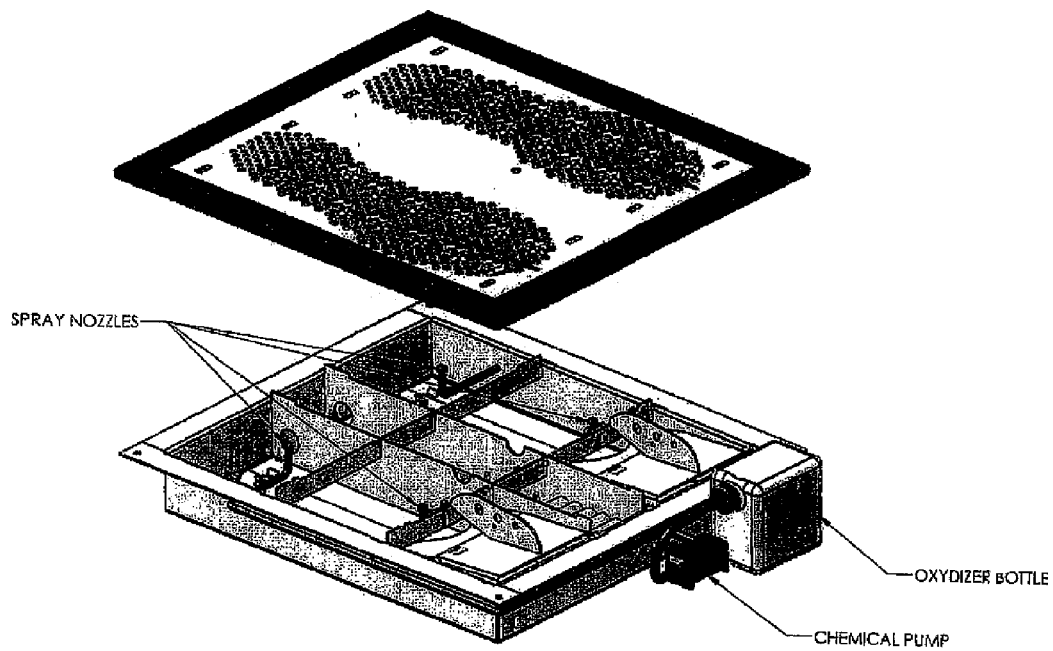
FIG. 3 is an exploded, perspective view of the shoe sole sanitizer incorporating an advanced oxidation system therein.

Referring to FIGS. 1 and 2, the sanitizing device is shown as a shoe sole sanitizer 100 wherein a UV radiation emitting device that kills microbial pathogens deposited on shoe sole surfaces. The shoe sole sanitizer is designed to reduce pathogens on or around the sole or outside of a sole. The shoe sole sanitizer can also be utilized to sterilize soles of feet, socks, and animal paws.

In an exemplary system, the shoe sole sanitizer 100 includes a housing 111 containing at least one UV radiation source 134. The source may be of any conventional emitter of germicidal energy having a wavelength for killing or inactivating microorganisms within the range of 180 nm-325 nm. Bottom and side portions of the housing are usually opaque to provide a UV shield while directing the UV upward towards top housing portion. The top housing portion includes a platform 94 that has a plurality of holes 104a and 104b that may form an approximate shape of two shoe sole bottoms, referred to herein as shoe sole approximation areas. The platform 94 is preferably metal. The housing can be made from any suitable material, such as metal and plastic, for example. The material can vary in type, thickness, and grade depending on the environment in which the device is being used, e.g., indoor or outdoor use, use in a food processing plant, an explosive environment, or in a wet area. Such materials can be adapted to make the device water resistant. The housing can be adapted to include either a manual or an automated cleaning system to maintain the device operating optimally. For example, the housing can include sensors to monitor the aging of the lamps and output of the device, as well as to increase or decrease power for optimal results.

The housing can also include various types of materials and disinfectants, such as hydrogen peroxide, to disinfect the shoe sole sanitizer and keep foreign matter from depositing inside the unit. The housing can be adapted to include brushes or mechanical devices to clean the footwear prior to use of the device. The housing can be used in conjunction with UV and/or ozone to produce an advanced oxidation result thereby increasing the germicidal process. FIGS. 3, 4, 4A, and 5 disclose an embodiment that incorporates an oxidation system into the housing.

The holes 104a and 104b allow UV radiation and/or advanced oxidation to escape the housing and target shoe sole surfaces disposed on and over the exterior of the housing top. The holes 104a and 104b also allow the shoe sole sanitizer 100 to adjust to any shoe size to reduce or eliminate unwanted UVC exposure onto surrounding persons or animals, surfaces, skin, or eyes. The holes 104a are disposed closer to a lateral edge of the platform 94 than the holes 104b. The holes 104a are of a smaller diameter than the holes 104b and are designed to let UV light through while acting as a physical barrier to prevent heels having small cross-sectional area (e.g., high heels) from sinking into the interior of the housing. The unintentional exposure of people to UVC light can also be controlled and prevented by the shoe print design on the top of the shoe sole sanitizer 100. For example, the UVC light may be transmitted to the soles of the user through the holes 104a and 104b and not from a remainder of the housing. A boot or sock mold can be used to delineate the area for the shoe so as to reduce or eliminate any unwanted UVC exposure. Portions of the housing 111 may be light reflective to aid in directing the UV source radiation through the holes 104a and 104b. The holes 104a and 104b can be located anywhere in the unit, such as the toe or heel region of the shoes or on the side areas of the shoes, thereby allowing the shoe sole sanitizer 100 to be used by a variety of people without having to worry about the variations in the shoe sizes and styles.

The holes 104a and 104b, as well as the shoe print design will enable the shoe sole sanitizer 100 to overcome many of the safety concerns raised by federal organizations such as the Food and Drug Administration (FDA) and the Occupational Safety and Health Administration (OSHA). The device 100 can be adapted to include safety switches, and sensors, such as pressure, proximity, and motion sensors, for example, to improve the safety and operation of the system. For example, a switch for activating the device 100 may be triggered only when weight exerted on the platform by a user exceeds a certain threshold value, e.g., 50 pounds. The switches and sensors can be placed on the top, the bottom, the sides, or below the top plate, so as to be used as a safety system to protect against misuse by children, pets, or infants. Additionally, the device can be adapted to include a timer to control exposure and operation of the device.

Extending vertically from a front sole portion of each shoe sole approximation area of platform 94, along a front centerline portion is a pivotal spring biased thin planar tang 102. Shutters 119 (shown in FIG. 2) attached internally to the tangs 102 extend or limit UV exposure from the platform 94 depending on whether the size and/or weight of the sole is large enough to depress the tang and thereby open the shutter admitting UV light close to the tangs 102 or small enough not to depress the tang thereby keeping the shutter in an elevated, closed position that forms a light barrier. The shutter 119 may be a mechanical or electronic shutter, for example, or other suitable type of shutter capable of reducing or eliminating the reflected light or direct UVC light from the UV source in the shoe sole sanitizer 100. Each shutter 119 is bifurcated and includes a pivotable flap extension 121. The spring biasing is achieved by a spring hinge 187 disposed through pivot holes 156 of the shutters 119 and pivot slots 157 of vertical barrier walls 136. Each shoe sole approximation area of the top has a pivotal tang that extends therefrom. The shutter system can be at the front of the sole or can be shaped to approximate the entire sole or any portion thereof. The shutter system may be a single shield or be segmented shields that encompass any desired design or configuration; and may be deployed singly or jointly. Additionally, with or without the shutter system, a template or shield may overlie the platform 94 and shield as much of the radiation as necessary thereby protecting users with small or odd shaped sole configurations.

Ridges 106 are disposed on the platform 94 along either side of the centerlines of the shoe sole approximation areas. These ridges 106 support the shoe soles so that a substantial portion of the shoe soles is elevated over the holes 104a, 104b thereby permitting a greater contact area of the UV radiation with the shoe soles and increase the area of a sole being exposed. Further, the ridges 106 can allow the shoe sole to be elevated and expose the shadowed areas of the shoe sole to the UVC light. The ridges 106 may also have through-bores allowing the UV radiation light to escape and contact portions of the shoe sole supported by ridges 106. Each ridge 106 can have a pair of through-bores, one through-bore on the right side of the ridge and another through-bore on the left side of the ridge.

Additionally, the top housing portion or platform 94 can be disposed as a recessed surface so that the shoe or foot is below the upper rim of the housing thereby permitting the germicidal energy to impact more of the side surfaces of the shoe or foot placed thereon in addition to the sole. Using the ridges with a platform 94 (FIGS. 1 and 2) or in a recessed configuration allows the use of UVC reflective materials thereby increasing the exposure of WC light onto otherwise shadowed areas of the sole or foot.

The system can be adapted to be operated automatically with the use of on/off timers or manually. The system can be powered by standard AC electrical power, battery sources, or solar power. A manually operated power switch 130 is disposed on the side of housing base 111 closest to a heel portion of the shoe sole approximation areas. Notwithstanding the manually operated power switch 130, a weight sensitive, timed exposure switch may also be employed for hands-free operation of the device 100. The UV sources 134 are preferably high cycling, quick start UV-C lamps, preferably of the elongated variety, and extending inside the housing beneath the shoe sole approximation area of holes 104a, 104b on the platform 94. For example, the UV sources can include light pipe sources, fiber optic sources, solid-state UVC sources, active and passive sensors arranged in a variety of configurations so as to control the UV light from escaping and instead focus, direct, or control the light onto a target. The cycling times of the lamps can be modified to increase the effectiveness of the device. Hot cathode, cold cathode, light emitting diodes, and induction UV lamps, as well as fiber optic and light pipes can be adapted for use in the housing to distribute the UVC light to the shoe sole. The UVC lamps preferably emit a substantial portion of photon energy at wavelength(s) somewhere between approximately 180 to approximately 325 nm. Ozone and ultrasonic energy disinfectants can be used in place of or in addition to the UVC lamps.

Elongate, rectangular circuit board 132 is disposed inside the housing 111 and enclosed by longitudinally disposed vertical barrier walls 136. Horizontal ribs 138 extend laterally perpendicular to the vertical barrier walls 136 and attach to the vertical barrier walls 136 via complementary slots disposed in the vertical barrier walls 136 and the horizontal ribs 138. Tabs on the ends of the horizontal ribs and complementary slots on the housing 111 secure the horizontal ribs 138 to the housing 111. Left side tabs extend toward the front of housing 111 and right side tabs extend toward the rear of housing 111. A translucent dust shield 97 is disposed below the support platform 94 and is supported by longitudinally extending dust shield retaining rods 84 which sit atop and perpendicular to the horizontal ribs 138. A flange 95 extends around the periphery of the support platform 94 and supports bezel 90.

The circuit board 132 shown in FIG. 2 can include an off-the-shelf Kodiak Tech, P69174 lamp ballast circuit. The circuit board 132 is designed to, upon application of power via power switch 130 and NiCad battery 199 produce a high voltage alternating current (AC) to the UV-C lamps which, in the embodiment shown, are the UV sources 134. The circuit board 132 is operably connected to an audible alert 166 to warn a user when the UV-C sources 134 are powered up and emitting UV-C radiation. An interlock switch 191 keeps the unit from powering on when the platform 94 is removed for servicing.

It is to be understood that the present invention is not limited to the embodiments described above, but encompasses any and all embodiments within the scope of the following claims.

We claim:

1. A device for sanitizing objects, comprising:
    a housing, the housing having longitudinal sides and lateral edges;
    a platform disposed in the housing, the platform having a top surface defining a front portion and a rearward portion, a bottom surface, longitudinal sides and lateral edges and being made of a material to permit light waves to travel therethrough;
    at least one ultraviolet (UV) light source disposed inside the housing and directing ultraviolet light waves through the platform;
    at least one pivotal spring biased planar tang vertically extending above at least the front portion of the platform and adapted to be engaged by a user of the device; and
    a shutter attached internally to the tang, the shutter being adjustable to allow UV light to escape the housing proximate the tang when the tang is depressed by the user and to block UV light from escaping the housing proximate the tang when the tang is released by the user.

2. The device for sanitizing objects according to claim 1, further comprising a pivotal flap extension that bifurcates each shutter.

3. The device for sanitizing objects according to claim 1, further comprising an audible alert disposed in the housing, the audible alert warning the user when the UV light source is powered up.

4. The device for sanitizing objects according to claim 1, further comprising a translucent dust shield attached to the housing and disposed between the housing interior and an underside portion of the platform.

5. The device for sanitizing objects according to claim 1, further comprising:
    a ballast circuit disposed in the housing, the ballast circuit powering the UV light source;
    a battery disposed in the housing; and
    a power switch connected to the battery, the power switch selectively applying power from the battery to the ballast circuit.

6. The shoe sole sanitizer according to claim 1, wherein the housing is substantially opaque.

7. The device for sanitizing objects according to claim 1, wherein portions of the housing are substantially light reflective to aid in directing the UV source radiation through the platform.

8. The device for sanitizing objects according to claim 1, wherein portions of the platform are substantially light reflective to aid in directing the UV source radiation through the platform.

9. The device for sanitizing objects according to claim 1, wherein the top surface of the platform is recessed within the housing so that an object placed on the platform is disposed below the upper surfaces of the longitudinal sides and lateral edges of the housing.

10. The device for sanitizing objects according to claim 1, further comprising a timer disposed in the housing to control exposure and operation of the device.

11. The device for sanitizing objects according to claim 1, wherein the ultraviolet (UV) light source is a UV-C lamp.

* * * * *